(12) United States Patent
Bashour (10) Patent No.: US 10,827,909 B2
(45) Date of Patent: Nov. 10, 2020

(54) ALIMENTARY ENGAGEMENT DEVICE

(71) Applicant: Fadi N. Bashour, Westlake, OH (US)

(72) Inventor: Fadi N. Bashour, Westlake, OH (US)

(73) Assignee: Marla F. Bashour, Westlake, OH (US)

( * ) Notice: Subject to any disclaimer, the term of this patent is extended or adjusted under 35 U.S.C. 154(b) by 403 days.

(21) Appl. No.: 15/896,657

(22) Filed: Feb. 14, 2018

(65) Prior Publication Data

US 2019/0246883 A1 Aug. 15, 2019

(51) Int. Cl.
*A61B 1/00* (2006.01)
*A61B 1/273* (2006.01)
*A61B 1/31* (2006.01)

(52) U.S. Cl.
CPC ...... *A61B 1/00154* (2013.01); *A61B 1/00082* (2013.01); *A61B 1/2733* (2013.01); *A61B 1/2736* (2013.01); *A61B 1/31* (2013.01)

(58) Field of Classification Search
CPC ........... A61B 1/00154; A61B 1/00082; A61B 1/2733; A61B 1/2736; A61B 1/31; A61B 5/6853; A61M 2025/1054; A61M 3/0295
See application file for complete search history.

(56) References Cited

U.S. PATENT DOCUMENTS

| | | | |
|---|---|---|---|
| 3,841,304 A | 10/1974 | Jones | |
| 4,040,413 A * | 8/1977 | Ohshiro | A61B 1/00082 600/116 |
| 4,451,256 A * | 5/1984 | Weikl | A61M 25/0668 604/164.03 |
| 4,648,384 A * | 3/1987 | Schmukler | A61M 1/3621 600/18 |
| 4,747,833 A * | 5/1988 | Kousai | A61M 25/0668 604/161 |
| 4,921,479 A * | 5/1990 | Grayzel | A61M 25/0668 604/160 |
| 5,147,316 A * | 9/1992 | Castillenti | A61B 17/34 604/164.04 |
| 5,171,222 A * | 12/1992 | Euteneuer | A61M 25/104 604/103.1 |
| 5,217,001 A * | 6/1993 | Nakao | A61B 1/00135 24/DIG. 50 |
| 5,259,366 A * | 11/1993 | Reydel | A61B 1/00135 383/203 |
| 5,267,958 A * | 12/1993 | Buchbinder | A61M 25/0029 604/103.05 |
| 5,315,992 A * | 5/1994 | Dalton | A61M 16/04 128/207.15 |

(Continued)

FOREIGN PATENT DOCUMENTS

FR 2896167 A1 7/2007

*Primary Examiner* — Timothy J Neal
*Assistant Examiner* — Jae Woo
(74) *Attorney, Agent, or Firm* — Emerson, Thomson & Bennett, LLC; Roger D. Emerson; Peter R. Detorre (57) ABSTRACT

Provided is an alimentary engagement device that may be used for certain medical procedures such as colonoscopies and endoscopies. The alimentary engagement device includes a conduit that is fitted over a medical instrument such as a colonoscope or an endoscope as it is inserted within a body cavity. On the outer surface of the conduit is a balloon which may be expanded to engage the walls within the interior of the cavity. The interior of the conduit includes a seal which has an aperture for allowing a medical instrument to pass through.

14 Claims, 7 Drawing Sheets

(56) References Cited

U.S. PATENT DOCUMENTS

| | | | | |
|---|---|---|---|---|
| 5,353,783 | A * | 10/1994 | Nakao | A61B 1/00135 600/106 |
| 5,368,567 | A * | 11/1994 | Lee | A61M 25/104 604/103.1 |
| 5,397,311 | A * | 3/1995 | Walker | A61M 25/0668 604/160 |
| 5,549,555 | A * | 8/1996 | Sohn | A61M 25/1002 604/101.01 |
| 5,746,694 | A * | 5/1998 | Wilk | A61B 1/121 600/121 |
| 5,762,604 | A * | 6/1998 | Kieturakis | A61B 17/00008 600/104 |
| 5,833,706 | A * | 11/1998 | St. Germain | A61M 25/104 606/194 |
| 5,879,337 | A * | 3/1999 | Kuracina | A61M 5/3243 604/192 |
| 5,882,334 | A * | 3/1999 | Sepetka | A61M 25/01 604/164.08 |
| 6,095,811 | A * | 8/2000 | Stearns | A61B 1/00142 433/116 |
| 6,569,085 | B2 * | 5/2003 | Kortenbach | A61B 1/00073 600/104 |
| 6,758,854 | B1 * | 7/2004 | Butler | A61M 25/0041 604/101.01 |
| 6,994,667 | B2 * | 2/2006 | Singh | A61B 1/0008 600/105 |
| 7,531,122 | B2 * | 5/2009 | Weber | B29O 65/18 264/403 |
| 7,578,831 | B2 * | 8/2009 | von Oepen | A61F 2/958 606/194 |
| 7,806,889 | B2 * | 10/2010 | Raulerson | A61M 25/0026 604/523 |
| 7,993,389 | B2 * | 8/2011 | Globerman | A61F 2/856 623/1.35 |
| 8,043,261 | B2 * | 10/2011 | Weststrate | A61B 17/3415 604/104 |
| 8,211,125 | B2 * | 7/2012 | Spivey | A61F 2/0063 606/108 |
| 8,979,805 | B1 * | 3/2015 | Khalaj | A61M 25/02 604/174 |
| 9,993,137 | B2 * | 6/2018 | Farhadi | A61B 1/00147 |
| 10,264,951 | B2 * | 4/2019 | Terliuc | A61B 1/00131 |
| 10,413,712 | B1 * | 9/2019 | Kuracina | A61M 25/0097 |
| 2002/0032457 | A1 * | 3/2002 | Sirhan | A61M 25/10 606/195 |
| 2003/0009151 | A1 * | 1/2003 | Wang | B29C 48/21 604/526 |
| 2004/0254528 | A1 * | 12/2004 | Adams | A61M 25/00 604/96.01 |
| 2008/0086192 | A1 * | 4/2008 | WasDyke | A61F 2/95 623/1.12 |
| 2009/0043287 | A1 * | 2/2009 | Mosler | A61M 25/00 604/544 |
| 2009/0076484 | A1 * | 3/2009 | Fukaya | A61M 25/0068 604/529 |
| 2010/0004730 | A1 * | 1/2010 | Benjamin | A61M 25/0662 623/1.11 |
| 2010/0177802 | A1 * | 7/2010 | Weyna | G01K 1/08 374/208 |
| 2010/0218849 | A1 * | 9/2010 | Hagano | B60K 15/04 141/350 |
| 2011/0105840 | A1 * | 5/2011 | Terliuc | A61B 1/00082 600/104 |
| 2011/0106014 | A1 * | 5/2011 | Helm, Jr. | A61M 25/02 604/178 |
| 2011/0108143 | A1 * | 5/2011 | Caluori | A47G 21/185 137/561 R |
| 2011/0208132 | A1 * | 8/2011 | Clark | A61M 39/12 604/257 |
| 2011/0251458 | A1 * | 10/2011 | Terliuc | A61B 8/445 600/116 |
| 2012/0101507 | A1 * | 4/2012 | Sloan | A61M 25/0668 606/108 |
| 2012/0184955 | A1 * | 7/2012 | Pivotto | A61B 34/74 606/41 |
| 2013/0184687 | A1 * | 7/2013 | Clark | A61M 39/1011 604/533 |
| 2013/0237952 | A1 * | 9/2013 | Takagi | A61M 37/00 604/500 |
| 2014/0051928 | A1 * | 2/2014 | Fouts | A61B 1/00154 600/114 |
| 2014/0114126 | A1 * | 4/2014 | Dresher | A61B 1/0125 600/106 |
| 2014/0128775 | A1 * | 5/2014 | Andreae | A61B 5/1405 600/581 |
| 2015/0328027 | A1 * | 11/2015 | Nishio | B29C 66/4322 156/218 |

* cited by examiner

ALIMENTARY ENGAGEMENT DEVICE

TECHNICAL FIELD

The present disclosure is directed to a device which is designed to engage the alimentary canal of an individual during medical procedures. The alimentary engagement device provides several advantages including preventing fluids from exiting the alimentary canal, preventing burns and perforations during medical procedures, providing enhanced visualization of the alimentary canal, and increasing the efficiency of medical procedures.

BACKGROUND

The present disclosure related to a medical device which may be used for various types of medical procedures involving the alimentary canal such as colonoscopies and endoscopies.

A colonoscopy is a common medical procedure for examining the large intestine (i.e., the colon). The procedure is typically used to screen for and detect bowel cancer and to diagnose various symptoms such as changes in bowel habits, abdominal pain, unexplained weight loss, iron deficiency, rectal bleeding, etc. In a colonoscopy, a physician or surgeon, inserts a colonoscope within an individual's colon. A colonoscope is a flexible tube having a fiber optic cable and a miniature camera on its end which allows the doctor to view the inside of the patient's colon. In addition to detecting and treating bowel cancer, colonoscopies may be used to determine the cause of abdominal pain, determine the cause of rectal bleeding, to stop intestinal bleeding, to take biopsies, to monitor a patient's response to treatment for inflammatory bowel disease and to determine the cause of a patient's change in bowel habits. Potential complications of colonoscopies include bleeding and perforation (i.e., a cut or tear) of the colon that allows air and intestinal material to leak into the abdominal cavity.

To obtain optimal visualization of the entire colonic mucosa, it is desirable to insufflate the colonic folds within the large intestine during a colonoscopy. However, in order for insufflation to be successful, there needs to be a device which blocks the passage of material out from the patient's colon. Accordingly, what is needed is a device which can act as a plug to both maintain insufflation of the colonic mucosa and a device which can act as an infection control measure by preventing a patient from unconsciously passing gas, fluid and excrement materials onto the operating scene during a colonoscopy. What is also needed is a device which can eliminate the need to re-insufflate a patient's colon should gas, fluid or excrement materials exit out from a patient's colon during a colonoscopy or similar medical procedure. The medical device or alimentary engagement device disclosed herein provides these advantages among others.

As mentioned above, in addition to colonoscopies, the medical device disclosed herein may also be used for a medical procedure referred to as an endoscopy. An endoscopy is a medical procedure which allows a doctor to view the mucosal lining of the upper portion of the gastrointestinal tract. Parts of the gastrointestinal tract that are viewed include the esophagus, stomach and duodenum. Upper endoscopies allow physicians to evaluate the cause of certain symptoms of the gastrointestinal tract such us upper abdominal pain, nausea, difficulty swallowing, vomiting and bleeding and are used to detect inflammation, infections, ulcers and tumors. Endoscopies are similar to colonoscopies in that a thin flexible fiber optic tube with a camera attached at an end of the tube is inserted within the alimentary canal through the patient's mouth moved through the throat until it reaches the areas to be evaluated within the digestive system including the esophagus, stomach and duodenum. Like colonoscopies, it is often desirable to introduce a small amount of air to flatten the mucosal lining within the gastrointestinal tract to improve visibility. As in colonoscopies, for insufflation to be successful, there needs to be a device which blocks the exit material such as air out from the patient's mouth. Accordingly, what is needed is a device which can be inserted within the patient's esophagus to act as a plug to maintain insufflation and to prevent air and other material from exiting the gastrointestinal tract during an endoscopy. What is also needed is a device which can eliminate the need to re-insufflate a patient's gastrointestinal tract during an endoscopy or similar medical procedure. The medical device or alimentary engagement device disclosed herein provides these advantages among others.

SUMMARY

Provided is an alimentary engagement device. The alimentary engagement device includes a conduit having an outer side surface having an outer circumference, an inner side surface having an inner circumference, an interior space, a first proximal end and a second distal end, wherein the cylindrical unit is fitted over a medical instrument that is inserted within a body cavity; a balloon attached to the outer side surface of the conduit; a balloon filling port having a first end connected to the balloon and a second end which extends from the balloon and exits the body cavity; and a seal within the interior space of the conduit, wherein the seal comprises an aperture for allowing a medical instrument to pass through.

According to further aspects of the present the disclosure, the conduit of the alimentary engagement includes a cylindrical unit.

According to further aspects of the present disclosure, the balloon of the alimentary engagement device is attached towards the second distal end of the cylindrical unit at a distance from the second distal end of the cylindrical unit.

According to further aspects of the present disclosure, the balloon is attached along the entire circumference of the cylindrical unit.

According to further aspects of the present disclosure, the cylindrical unit includes a joint which extends from the first proximal end to the second distal end of the cylindrical unit and an openable portion which extends from the first proximal end to the second distal end of the cylindrical unit, wherein the joint and openable portion allows the cylindrical unit to be adjusted between a first open configuration and a second closed configuration, wherein the first open configuration allows the interior space of the cylindrical unit to receive a medical instrument through the openable portion and the second closed configuration allows the cylindrical unit to engage the medical instrument.

According to further aspects of the present disclosure, the cylindrical unit includes a first half and a second half, wherein the first half and second half of the cylindrical unit are connected together by the joint.

According to further aspects of the present disclosure, the balloon filling port is formed from a rubber tube. According to further aspects of the present disclosure, the balloon filling port extends about 60 cm outside of a patient's body.

According to further aspects of the present disclosure, the second end of the conduit is connected to a pump for filling the balloon with fluid.

According to further aspects of the present disclosure, the seal comprises a first half and a second half, wherein the first half of the seal is attached to the first half of the cylindrical unit and second half of the seal is attached to the second half of the cylindrical unit.

According to further aspects of the present disclosure, the seal is openable and closable with the first half and second half of the cylindrical unit.

According to further aspects of the present disclosure, the seal is attached towards the second distal end of the cylindrical unit at a distance from the second distal end of the cylindrical unit.

According to further aspects of the present disclosure, the seal is in the form of sealing flaps.

According to further aspects of the present disclosure, the balloon is positioned below the sealing flaps.

According to further aspects of the present disclosure, the openable portion of the cylindrical unit includes a first side and a second side, wherein the first side includes at least one locking tab and the second side includes at least one tab receiving aperture.

According to further aspects of the present disclosure, the first side of the openable portion of the cylindrical unit comprises three locking tabs and the second side of the openable portion of the cylindrical unit comprises three tab receiving apertures.

According to further aspects of the present disclosure, the cylindrical unit has a length of about 6 cm and the balloon has a diameter of about 6 cm in its expanded state.

According to further aspects of the present disclosure, the cylindrical unit has a length of about 30 cm and the balloon has a diameter of about 4 cm.

According to further aspects of the present disclosure, the medical instrument is a colonoscope.

According to further aspects of the present disclosure, the medical instrument is an endoscope.

Also provided is a method of using an alimentary engagement device. The method includes the following order of steps: inserting a medical instrument into a patient's alimentary canal, applying the alimentary engagement device in an open configuration to a portion of the probe that extends outside of a patient's body, closing the alimentary engagement device, sliding the alimentary engagement device along the probe inside of the patient to a desired position within the alimentary canal, and activating a pump to fill the balloon within the alimentary engagement device to engage the patient's alimentary canal.

BRIEF DESCRIPTION OF THE DRAWINGS

The accompanying drawings in the following description illustrate various exemplary embodiments of the present disclosure. It is understood that a person of ordinary skill in the art may derive other embodiments from these drawings which fall within the scope of the disclosure set forth herein.

DETAILED DESCRIPTION

The present disclosure is directed to an alimentary engagement device which is capable of engaging sections of the alimentary canal within both the upper and lower gastrointestinal tract. The device is useful for colonoscopies, endoscopies and other medical procedures which involve the insertion of a probe, catheter or other instrument into a patient's colon or large intestine within a patient's lower gastrointestinal tract or into a patient's esophagus, stomach and duodenum within a patient's upper gastrointestinal tract.

Figure 1:
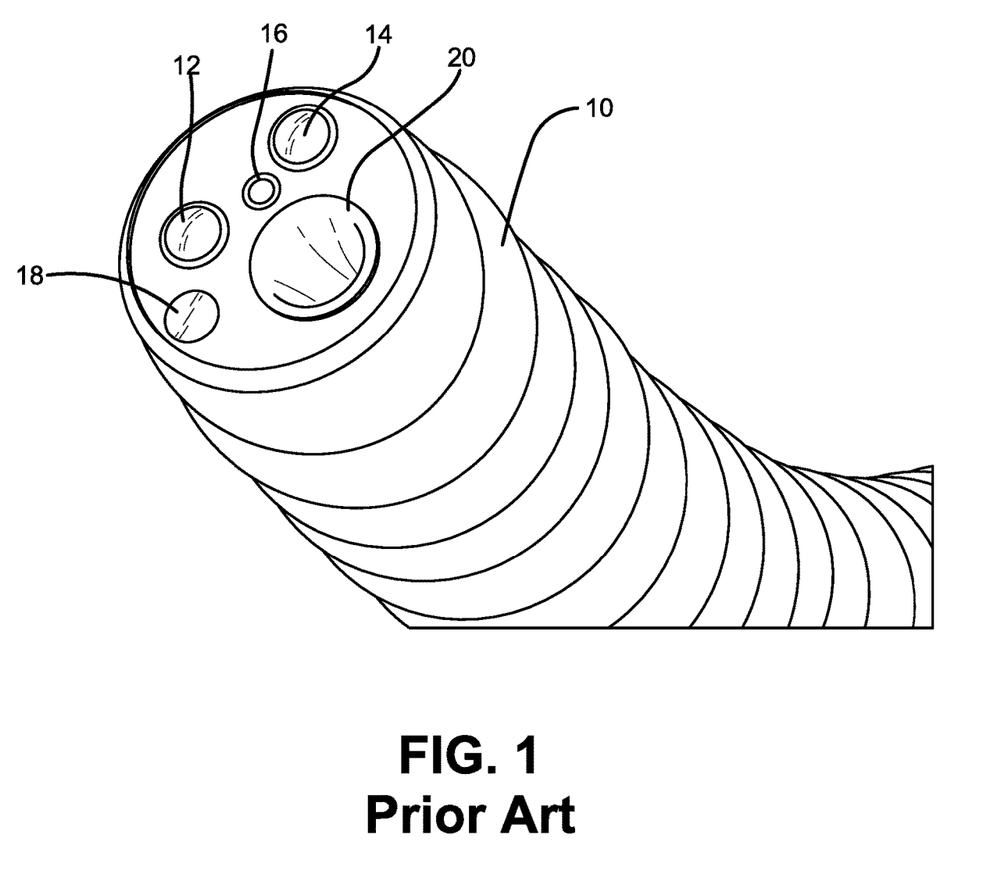
FIG. 1 is a first perspective view of an alimentary engagement device in an open unassembled configuration.

A colonoscopy is a medical procedure where a colonoscope is inserted into a patient's large intestine through the patient's rectum. An endoscopy is a somewhat similar procedure where an endoscope is inserted into a patient's upper gastrointestinal tract through the patient's mouth. Colonoscopies allow a gastroenterologist to view the patient's colon whereas endoscopies allow a gastroenterologist to view a patient's esophagus, stomach and duodenum. Colonoscopes and endoscopes are thin flexible tubes that include several channels. An example of a typical colonoscope/endoscope (10) is provided within FIG. 1. One channel of the colonoscope/endoscope tube (10) includes a fiber optic cable that is connected to a video camera (12) at the end of the tube. A second channel provides a connection to a light (14) at the end of the tube. The video camera (12) and light (14) operate in conjunction to transmit images of a patient's alimentary canal to a monitor or computer screen so that a doctor can view the patient's gastrointestinal tract in real time. Other channels which may be included within the tube are a water jet channel (16), an air/water channel (18) and an instrument channel (20). The water jet channel (16) (also referred to as an irrigation channel) houses a water jet that is used to flush water or air into the alimentary canal (e.g., the colon, esophagus, stomach or duodenum). This is used to clean debris from the colon or upper gastrointestinal tract to allow the physician or gastroenterologist to more clearly see what the inside of the alimentary canal on the monitor. This can make it easier for the gastroenterologist to confirm the presence or absence of polyps. If polyps are present, a tool may be inserted through the instrument channel (20) to remove the polyp. Examples of such tools include but are not limited to forceps, wired loops and snares. These tools may be used to take a biopsy by removing the polyp or other suspicious tissue from the alimentary canal. The biopsied tissue may then be evaluated for signs of cancer. During the procedure, the gastroenterologist may inject air into the lower gastrointestinal tract (e.g., the colon) or upper gastrointestinal tract (e.g., the esophagus, stomach or duodenum) through the air/water channel (18) to insufflate folds within the gastrointestinal tract (e.g., colonic folds or gastric folds). This allows the gastroenterologist to obtain a better view of a particular area within the alimentary canal.

Unfortunately, air which is injected within the colon or upper digestive tract of a patient during a colonoscopy or endoscopy has a tendency to leak out of the gastrointestinal tract. This can make it difficult for the gastroenterologist to view the inside of the alimentary canal. As a result, the gastroenterologist may need to re-insufflate the alimentary canal (e.g., the colon or stomach) in order to obtain a better image of the gastrointestinal tract. This is an inefficient process as additional time must be spent re-insufflating the gastrointestinal tract which results in the patient undergoing a longer procedure. If an accurate image cannot be obtained, the procedure can also result in the gastroenterologist missing a polyp or area of concern resulting in an inaccurate diagnosis. Moreover, air which has leaked out of a patient's lower or upper gastrointestinal tract results in diminishing the size of the area which surrounds colonic and gastric folds. This can make surgical procedures such as a polpectomy that take place during a colonoscopy, endoscopy or other medical procedure more difficult. As a result, the patient may experience deep burns or perforations within the gastrointestinal lining as the gastroenterologist removes polyps and/or takes biopsies.

The alimentary engagement device disclosed herein is capable of resolving these problems which are associated with colonoscopies, endoscopies and similar medical procedures. An exemplary embodiment of an alimentary engagement device (22) is illustrated within FIGS. 2 through 5. As shown within FIGS. 2 through 5, the alimentary engagement device (22) includes a conduit (24) which fits around a medical instrument such as a colonoscope/endoscope (10) that is inserted within a body cavity. The conduit (24) may be described as having an outer side surface (26) having an outer circumference, an inner side surface (28) having an inner circumference and an interior space (30). According to certain aspects of the present teaching, the conduit (24) may be a cylindrical unit. However, the conduit may be any shape as deemed suitable by a person of ordinary skill in the art. Accordingly, the terms conduit and cylindrical unit are used interchangeably throughout this disclosure. The cylindrical unit (24) may also be described as having a first proximal end (32) and a second distal end (34).

The cylindrical unit (24) includes a balloon (36) which attached to the outer side surface (26). The balloon (36) may be attached at any point along the length of the cylindrical unit (24). However, according to certain aspects of the present teaching, the balloon (36) is attached towards the second distal end (34) of the cylindrical unit (24) at a distance from the first proximal end (32) of the cylindrical unit (24). The balloon (36) may also be designed to cover any portion of the cylindrical unit (24). According to certain aspects of the present teaching, the balloon (36) is attached to and covers the entire circumference of the cylindrical unit (24).

Extending downward from the balloon (36) is a balloon filling port (38). The balloon filling port (38) has a first end which is connected to the balloon (36) and a second end which extends from the balloon and exits the body cavity. The second end of the balloon filling port (38) may be connected to a pump for filling the balloon with fluid such as air to seal the patient's alimentary canal. According to certain aspects of the present disclosure, the balloon filling port (38) is a rubber tube. However, it is to be understood that the balloon filling port may be manufactured from any material deemed suitable by a person of ordinary skill in the art. The balloon filling port may be any length as required for use during the medical procedure. For example, according to certain aspects of the present disclosure, the balloon filling port may extend about 60 cm out of a patient's body. The balloon filling port may also be clipped to a bed. This can minimize the risk of an accidental slippage inside of a patient's rectum during a colonoscopy which can lead to leakage of air below the balloon.

According to further aspects of the present teaching, the alimentary engagement device (22) includes a joint (42) which extends from the first proximal end (32) to the second distal end (34) of the cylindrical unit or conduit (24) and an openable portion (44) opposite the joint (42) which extends from the first proximal end (32) to the second distal end (34) of the cylindrical unit or conduit (24). The joint (42) and openable portion (44) divides the cylindrical unit (24) into a first half (46) and a second half (48). The first half (46) of the cylindrical unit (24) has a first side (50) and the second half (48) of the cylindrical unit (24) has a second side (52) which forms an openable portion opposite the joint (42). The joint (42) and openable portion (44) work in conjunction to allow the cylindrical unit (24) to be adjusted between a first open configuration shown in FIGS. 2 and 3 and a second closed configuration shown in FIGS. 4 and 5. In the open configuration, the first half (46) and second half (48) of the cylindrical unit (24) are connected together by the joint (42). In the closed configuration, the first half (46) and second half (48) of the cylindrical unit (24) are connected together by both the joint (42) and closed openable portion (44). When in the open configuration, the interior space (30) of the cylindrical unit or conduit is accessible, allowing the openable portion (44) of the cylindrical unit (24) to receive a medical instrument such as a colonoscope/endoscope. Once the user inserts the medical instrument within the cylindrical unit (24), the cylindrical unit (24) may be adjusted into the closed configuration. The closed configuration allows the cylindrical unit to engage the medical instrument (e.g., colonoscope/endoscope) in a secure manner so that it does not slide with respect to the medical instrument.

According to further aspects of the present teaching, the alimentary engagement device (22) includes a joint (42) which extends from the first proximal end (32) to the second distal end (34) of the cylindrical unit or conduit (24) and an openable portion (44) opposite the joint (42) which extends from the first proximal end (32) to the second distal end (34) of the cylindrical unit or conduit (24). The joint (42) and openable portion (44) divides the cylindrical unit (24) into a first half (46) and a second half (48). The first half (46) of the cylindrical unit (24) has a first end (50) and the second half (48) of the cylindrical unit (24) has a second end (52) which forms an openable portion opposite the joint (42). The joint (42) and openable portion (44) work in conjunction to allow the cylindrical unit (24) to be adjusted between a first open configuration shown in FIGS. 2 and 3 and a second closed configuration shown in FIGS. 4 and 5. In the open configuration, the first half (46) and second half (48) of the cylindrical unit (24) are connected together by the joint (42). In the closed configuration, the first half (46) and second half (48) of the cylindrical unit (24) are connected together by both the joint (42) and closed openable portion (44). When in the open configuration, the interior space (30) of the cylindrical unit or conduit is accessible, allowing the openable portion (44) of the cylindrical unit (24) to receive a medical instrument such as a colonoscope/endoscope. Once the user inserts the medical instrument within the cylindrical unit (24), the cylindrical unit (24) may be adjusted into the closed configuration. The closed configuration allows the cylindrical unit to engage the medical instrument (e.g., colonoscope/endoscope) in a secure manner so that it does not slide with respect to the medical instrument.

The cylindrical unit (24) may also include at least one locking tab (54) at one side of the openable portion (44) of the cylindrical unit (24) and at least one corresponding locking tab receiving aperture (56) at the opposing side of the openable portion (44) of the cylindrical unit (24). The locking tab (54) and receiving aperture (56) may work in conjunction to allow the cylindrical unit (24) to be locked and secured into the closed configuration when engaging a medical instrument such as a colonoscope or endoscope. According to certain aspects of the present disclosure, one side of the openable portion (44) of the cylindrical unit (24) includes three locking tabs (54) and the opposing side of the openable portion (44) of the cylindrical unit (24) includes three corresponding tab receiving apertures (56) to lock and secure the cylindrical unit (24) in a closed configuration.

As mentioned above, the alimentary engagement device (22) may be used to engage a colonoscope for a colonoscopy or to engage an endoscope for an endocscopy. With respect to endoscopies, the alimentary engagement device (22) may be used to perform an upper endoscopy in patients having large hiatal hernias where maintaining insufflation of the stomach is a challenge. In embodiments where the alimentary engagement device (22) is used for colonoscopies, the cylindrical unit (24) may have a length of about 6 cm and the balloon may have a diameter of about 6 cm. In embodiments where the alimentary engagement device is used for endoscopies, the cylindrical unit may have a length of about 30 cm and the balloon may have a diameter of about 4 cm.

Figure 2:
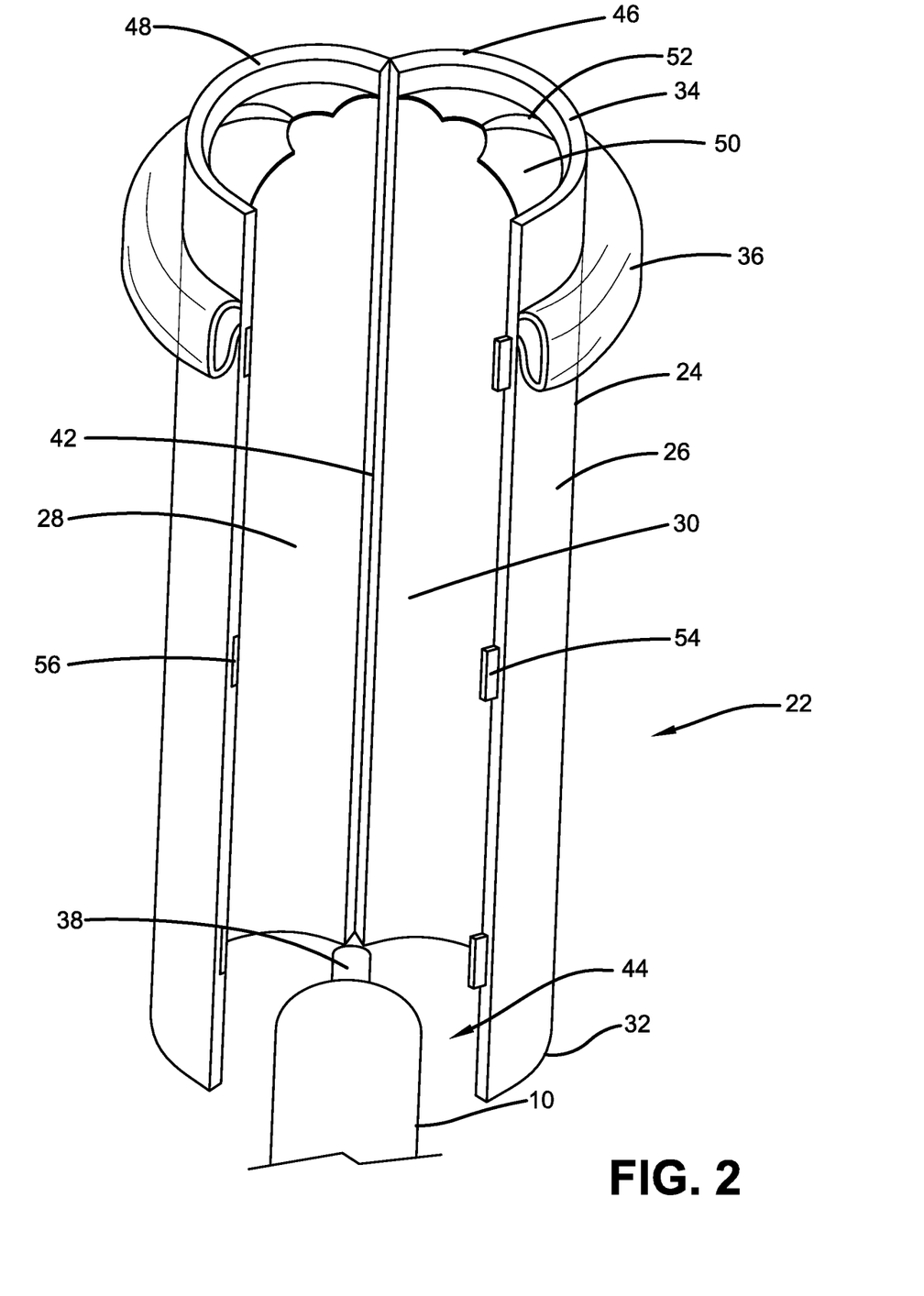
FIG. 2 is a second perspective view of an alimentary engagement device in an open unassembled configuration.
Figure 3:
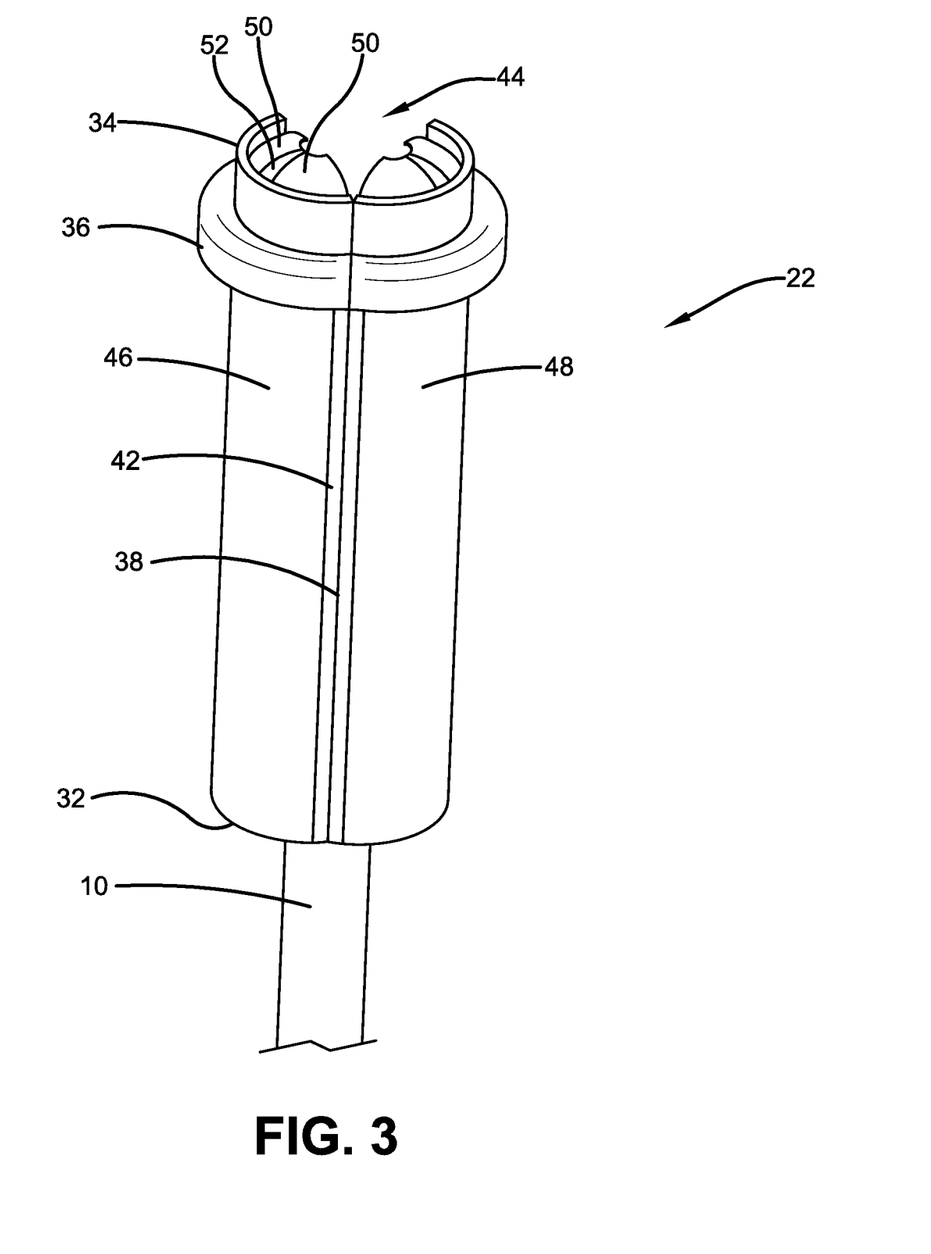
FIG. 3 is a first perspective view of an alimentary engagement device in a closed assembled configuration.
Figure 4:
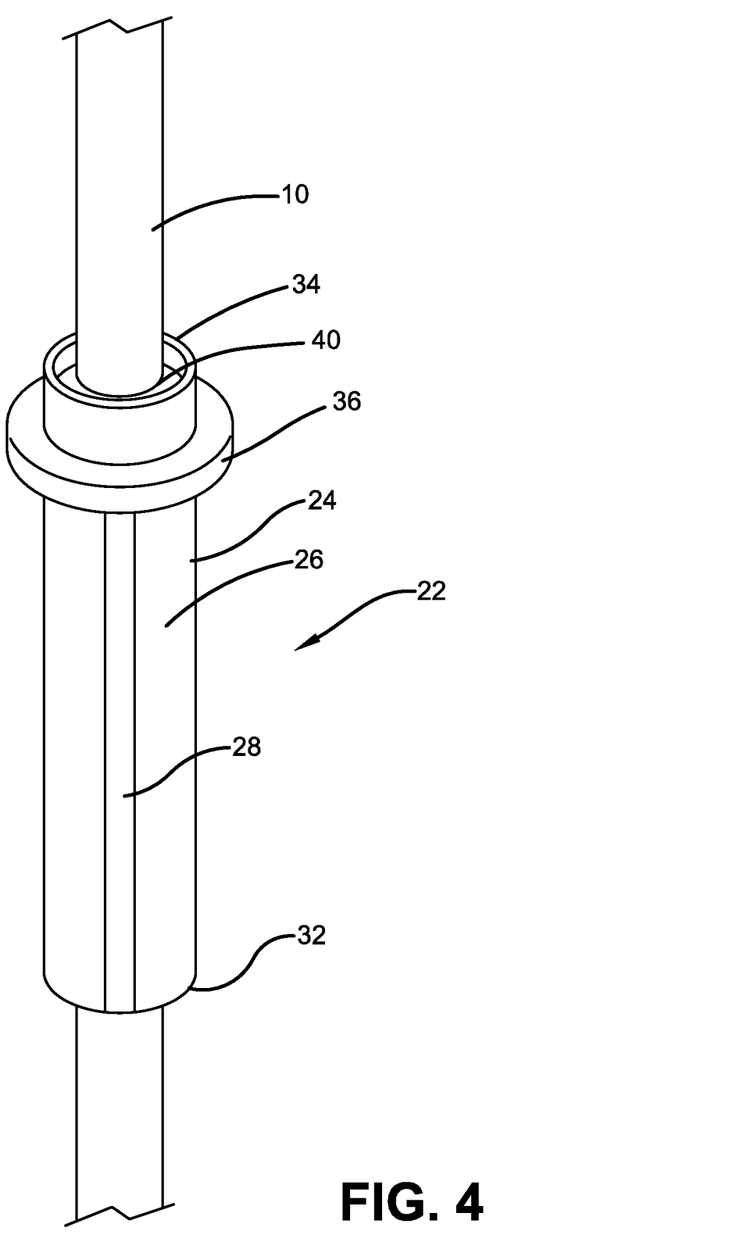
FIG. 4 is a second perspective view of an alimentary engagement device in a closed assembled configuration.
Figure 5:
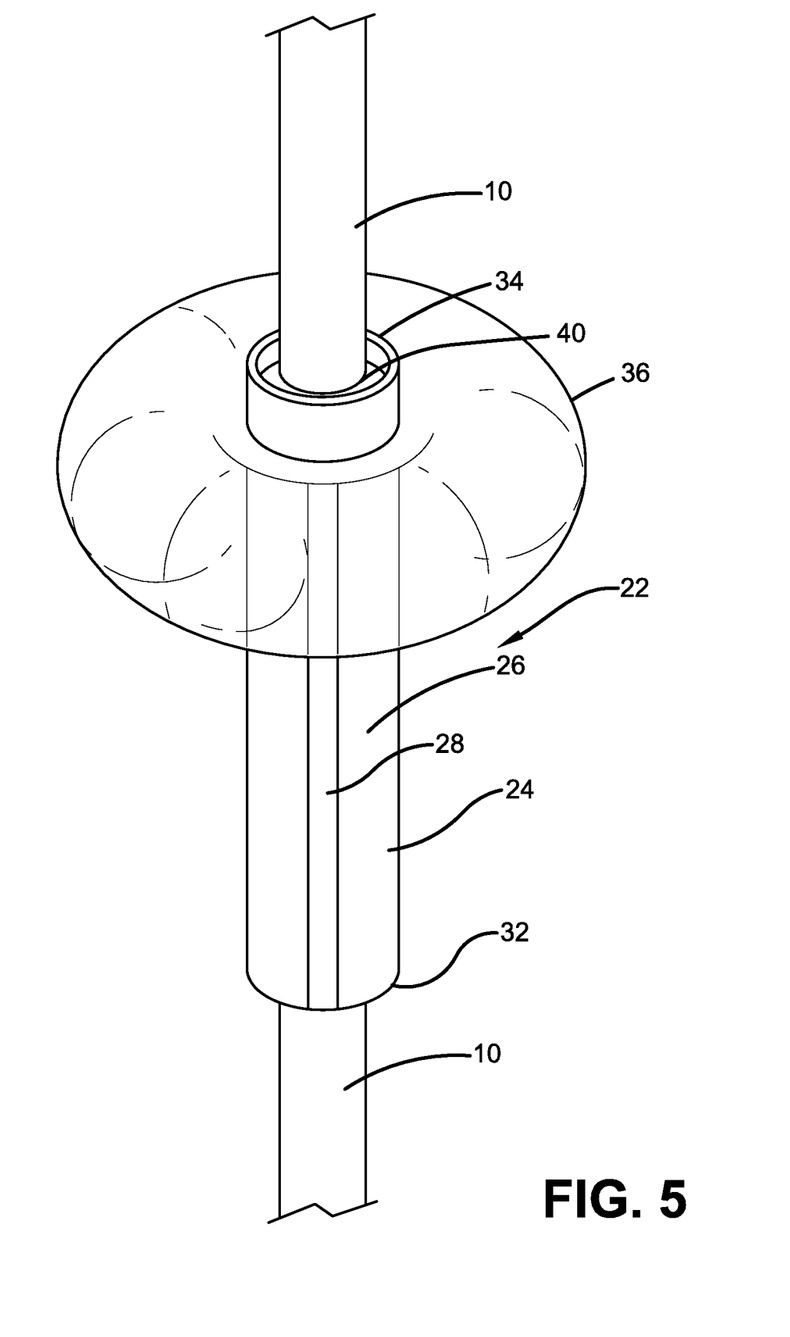
FIG. 5 is a planar view of an endoscope inserted within the upper digestive tract of a human being.
Figure 6:
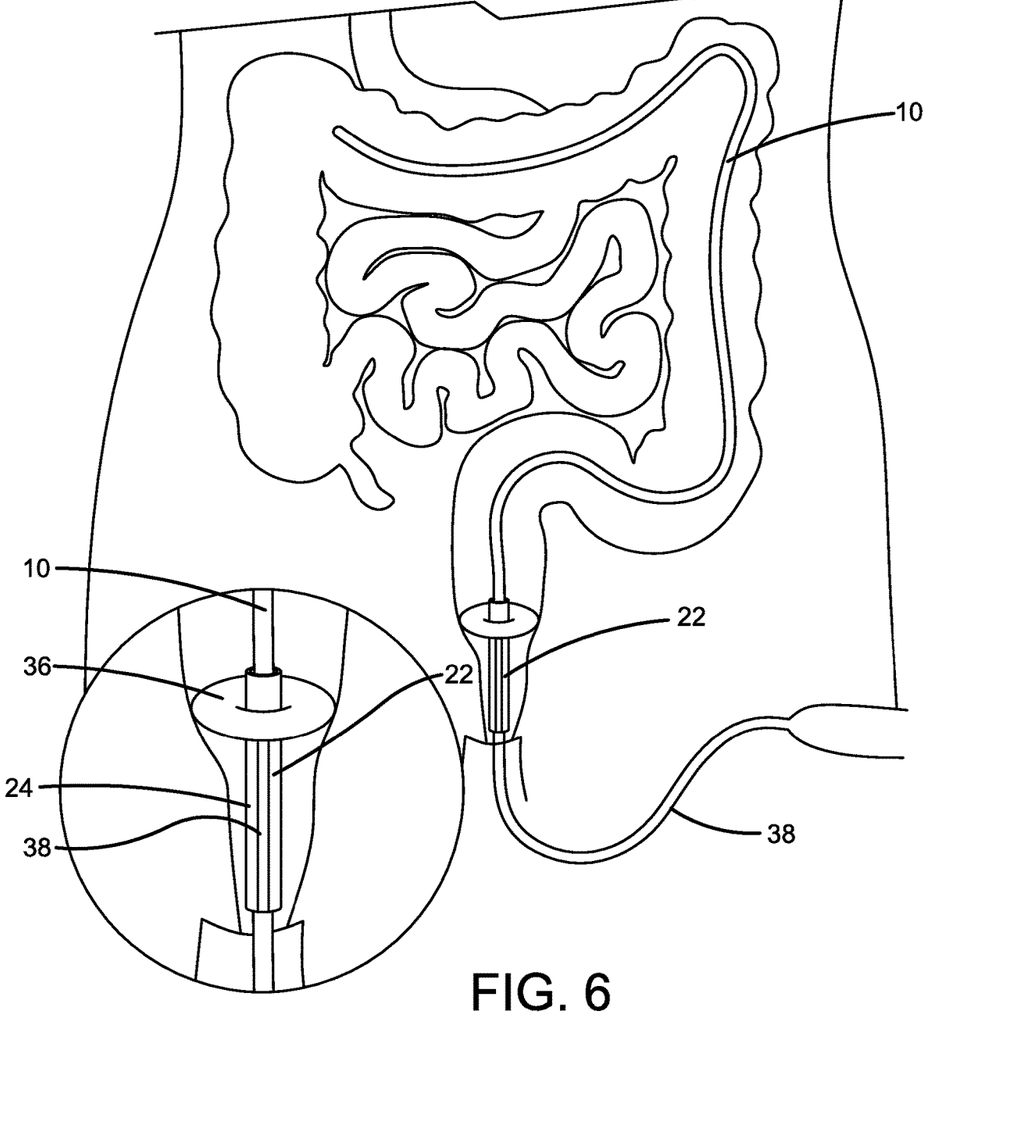
FIG. 6 is view of an alimentary engagement device inserted within an individual's lower digestive tract.
Figure 7:
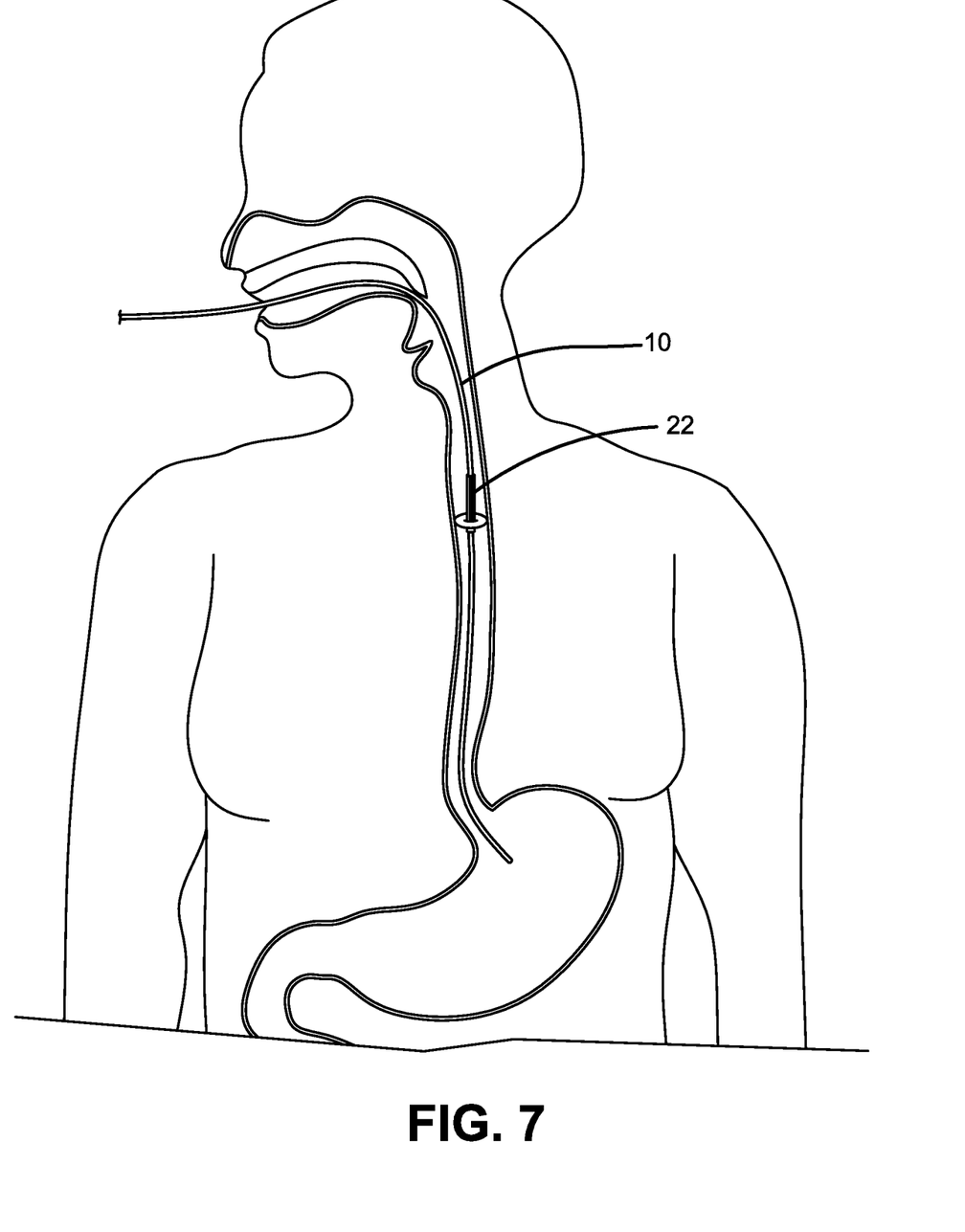
FIG. 7 is a view of an alimentary engagement device inserted within an individual's upper digestive tract.

As mentioned above, interior space (30) of the cylindrical unit or conduit (24) may include a seal (40) connected to or integral with the interior portion of the cylindrical unit or conduit (24) for closing a gap between the inner side surface (28) of the cylindrical unit or conduit (24) and the medical instrument (e.g., a colonoscope/endoscope). According to certain aspects of the present teaching, the seal (40) may be formed from the combination and overlapping of several sealing flaps (50) as the cylindrical unit (24) transitions from an open configuration to a closed configuration. The sealing flaps (50) may be separated by a space (52) between each sealing flap (50) when in the open configuration. Upon transitioning the cylindrical unit (24) from an open to a closed configuration, the space (52) between each sealing flap (50) closes so that a continuous seal (40) is formed. This is illustrated within FIGS. 2 through 4. Forming a seal from sealing flaps provides a certain degree of flexibility to the seal allowing for sliding movement of the medical instrument within the cylindrical unit or conduit when in the closed or engaged configuration. The seal flaps may be connected, attached or integral with the inner side surface (28) of the first half (46) and the second half (48) of the cylindrical unit (24). The seal (40) is openable and closable with the first half (46) and the second half (48) of the cylindrical unit (24). This is illustrated within FIGS. 2 through 5 wherein FIGS. 2 and 3 show the seal (40) in an opened configuration and FIGS. 4 and 5 show the seal (40) in a closed configuration. The seal (40) or sealing flaps (50) may be positioned at any point along the length of the cylindrical unit or conduit (24) as deemed suitable. In the embodiment illustrated within FIGS. 2 through 5, the sealing flaps (50) and seal (40) is positioned towards the second distal end (34) of the cylindrical unit (24) at a certain distance from the first proximal end (32) of the cylindrical unit (24). Moreover, according to further aspects of the present disclosure, the seal (40) and sealing flaps (50) may be positioned along the interior of the cylindrical unit or conduit (24) above the balloon (36) or closer to the second distal end of the cylindrical unit (24) than the balloon (36).

Also provided is a method of using an alimentary engagement for medical procedures such as colonoscopies and endoscopies. The method includes the steps of inserting a probe or other medical device or instrument into a patient's alimentary canal, applying an alimentary engagement device in an open configuration to a portion of the probe that extends outside of the patient's body, closing the alimentary engagement device, sliding the alimentary engagement device along the probe inside of the patient to a desired position within the alimentary canal, and activating a pump to fill a balloon within the alimentary engagement device to engage the patient's alimentary canal.

While the alimentary engagement device provided herein has been described in connection with various illustrative embodiments, it is to be understood that other similar embodiments may be used or modifications and additions may be made to the described embodiments for performing the same function disclosed herein without deviating therefrom. Further, all embodiments disclosed are not necessarily in the alternative, as various embodiments may be combined or subtracted to provide the desired characteristics. Variations can be made by one having ordinary skill in the art without departing from the spirit and scope hereof. Therefore, the alimentary engagement device should not be limited to any single embodiment, but rather construed in breadth and scope in accordance with the recitations of the appended claims.

What is claimed is:

1. An alimentary engagement device comprising:
a cylindrical unit having an outer side surface having an outer circumference, an inner side surface having an inner circumference, an interior space, a first proximal end and a second distal end,
wherein the cylindrical unit is fitted over a medical instrument that is inserted within a body cavity,
wherein the cylindrical unit comprises a joint which extends from the first proximal end to the second distal end of the cylindrical unit and an openable portion which extends from the first proximal end to the second distal end of the cylindrical unit,
wherein the cylindrical unit comprises a first half and a second half, wherein the first half and second half of the cylindrical unit are connected together by the joint,
wherein the joint and openable portion allow the cylindrical unit to be adjusted between a first open configuration and a second closed configuration,
wherein the openable portion of the cylindrical unit comprises a first side and a second side, wherein the first side comprises at least one locking tab and the second side comprises at least one tab receiving aperture,
wherein the first open configuration allows the interior space of the cylindrical unit to receive a medical instrument through the openable portion and the second closed configuration allows the cylindrical unit to engage the medical instrument;
a balloon attached to the outer side surface of the cylindrical unit;
a balloon filling port having a first end connected to the balloon and a second end which extends from the balloon and exits the body cavity; and
a seal within the interior space of the cylindrical unit, wherein the seal comprises an aperture for allowing a medical instrument to pass through, wherein the seal comprises a first half and a second half, wherein the first half of the seal is attached to the first half of the cylindrical unit and the second half of the seal is attached to the second half of the cylindrical unit, wherein the seal is openable and closable with the first half and second half of the cylindrical unit, wherein the cylindrical unit does not include any working channels.

2. The alimentary engagement device of claim 1, wherein the balloon is attached towards the second distal end of the cylindrical unit at a distance from the first proximal end of the cylindrical unit.

3. The alimentary engagement device of claim 2, wherein the balloon is attached along the entire circumference of the cylindrical unit.

4. The alimentary engagement device of claim 1, wherein the balloon filling port comprises a rubber tube and wherein the balloon filling port extends outside of a patient's body.

5. The alimentary engagement device of claim 4, wherein the balloon filling port is connected to a pump for filling the balloon with fluid.

6. The alimentary engagement device of claim 1, wherein the seal is attached towards the second distal end of the cylindrical unit at a distance from the first proximal end of the cylindrical unit.

7. The alimentary engagement device of claim 6, wherein the seal comprises sealing flaps.

8. The alimentary engagement device of claim 7, wherein the balloon is positioned proximal the sealing flaps.

9. The alimentary engagement device of claim 1, wherein the first side of the openable portion of the cylindrical unit comprises three locking tabs and the second side of the openable portion of the cylindrical unit comprises three tab receiving apertures.

10. The alimentary engagement device of claim 1, wherein the cylindrical unit has a length of about 6 cm and the balloon has a diameter of about 6 cm in its expanded state.

11. The alimentary engagement device of claim 1, wherein the cylindrical unit has a length of about 30 cm and the balloon has a diameter of about 4 cm.

12. The alimentary engagement device of claim 1, wherein the medical instrument is a colonoscope.

13. The alimentary engagement device of claim 1, wherein the medical instrument is an endoscope.

14. A method of using the alimentary engagement device of claim 1, wherein the method comprises the following order of steps:
  i) inserting the medical instrument into a patient's alimentary canal,
  ii) applying the alimentary engagement device in an open configuration to a portion of a probe that extends outside of a patient's body,
  iii) closing the alimentary engagement device,
  iv) sliding the alimentary engagement device along the probe inside of the patient to a desired position within the alimentary canal, and
  v) activating a pump to fill the balloon within the alimentary engagement device to engage the patient's alimentary canal.

* * * * *